(12) United States Patent
Cinbis et al.

(10) Patent No.: US 8,515,537 B2
(45) Date of Patent: *Aug. 20, 2013

(54) TISSUE OXYGENATION MONITORING IN HEART FAILURE

(75) Inventors: Can Cinbis, Shoreview, MN (US); James K. Carney, Brooklyn Park, MN (US); Jonathan L. Kuhn, Ham Lake, MN (US); David A. Anderson, Stanchfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 280 days.

This patent is subject to a terminal disclaimer.

(21) Appl. No.: 12/797,823

(22) Filed: Jun. 10, 2010

(65) Prior Publication Data

US 2010/0317947 A1 Dec. 16, 2010

Related U.S. Application Data

(60) Provisional application No. 61/185,812, filed on Jun. 10, 2009.

(51) Int. Cl.
*A61N 1/00* (2006.01)
(52) U.S. Cl.
USPC .......................................................... 607/17
(58) Field of Classification Search
USPC .............................. 600/324, 473; 607/17–23
See application file for complete search history.

(56) References Cited

U.S. PATENT DOCUMENTS

| | | | |
|---|---|---|---|
| 4,180,078 A | 12/1979 | Anderson | |
| 4,202,339 A | 5/1980 | Wirtzfeld et al. | |
| 4,230,122 A | 10/1980 | Lubbers et al. | |
| 4,399,820 A | 8/1983 | Wirtzfeld et al. | |
| 4,467,807 A | 8/1984 | Bornzin | |
| 4,548,209 A | 10/1985 | Wielders et al. | |
| 4,567,892 A | 2/1986 | Plicchi et al. | |
| 4,750,495 A | 6/1988 | Moore et al. | |
| 4,967,748 A | 11/1990 | Cohen | |
| 5,007,423 A | 4/1991 | Branstetter et al. | |
| 5,163,427 A | 11/1992 | Keimel | |
| 5,176,137 A | 1/1993 | Erickson et al. | |

(Continued)

FOREIGN PATENT DOCUMENTS

| EP | 760476 | 3/1997 |
|---|---|---|
| EP | 1764034 | 3/2007 |

(Continued)

OTHER PUBLICATIONS (PCT/US2010/038116) PCT Notification of Transmittal of the International Search Report and the Written Opinion of the International Searching Authority, Mailed Oct. 6, 2010, 8 pages.

(Continued)

*Primary Examiner* — Tse Chen
*Assistant Examiner* — Hien Nguyen
(74) *Attorney, Agent, or Firm* — Evans M. Mburu

(57) ABSTRACT

A medical device system and associated method control the delivery of a therapy to a patient. The system includes an activity sensor and detects a change in activity level of the patient. The system further include an optical sensor to sense signal corresponding to tissue light attenuation. The system computes a tissue oxygenation measurement in response to detecting a change in activity level. A parameter controlling delivery of the therapy is adjusted in response to detecting the decreased tissue oxygenation.

23 Claims, 6 Drawing Sheets

(56) References Cited

U.S. PATENT DOCUMENTS

| | | |
|---|---|---|
| 5,188,105 A | 2/1993 | Keimel |
| 5,188,108 A | 2/1993 | Secker |
| 5,193,535 A | 3/1993 | Bardy et al. |
| 5,213,098 A | 5/1993 | Bennett |
| 5,218,962 A | 6/1993 | Mannheimer et al. |
| 5,227,181 A | 7/1993 | Knudsen |
| 5,354,316 A | 10/1994 | Keimel |
| 5,364,316 A | 11/1994 | Brambilla |
| 5,385,143 A | 1/1995 | Aoyagi |
| 5,398,680 A | 3/1995 | Polson et al. |
| 5,431,172 A | 7/1995 | Hoegnelid et al. |
| 5,464,434 A | 11/1995 | Alt |
| 5,470,345 A | 11/1995 | Hassler et al. |
| 5,531,714 A | 7/1996 | Dahn et al. |
| 5,545,186 A | 8/1996 | Olson et al. |
| 5,588,427 A | 12/1996 | Tien |
| 5,593,431 A | 1/1997 | Sheldon |
| 5,596,986 A | 1/1997 | Goldfarb |
| 5,683,432 A | 11/1997 | Goedeke et al. |
| 5,752,519 A | 5/1998 | Benaron et al. |
| 5,769,785 A | 6/1998 | Diab et al. |
| 5,855,593 A | 1/1999 | Olson et al. |
| 5,879,294 A | 3/1999 | Anderson et al. |
| 5,902,326 A | 5/1999 | Lessar et al. |
| 6,144,866 A | 11/2000 | Miesel et al. |
| 6,198,952 B1 | 3/2001 | Miesel et al. |
| 6,226,540 B1 | 5/2001 | Bernreuter |
| 6,236,882 B1 | 5/2001 | Lee et al. |
| 6,292,698 B1 | 9/2001 | Duffin et al. |
| 6,377,840 B1 | 4/2002 | Gritsenko et al. |
| 6,473,632 B1 | 10/2002 | Myers |
| 6,481,899 B1 | 11/2002 | Quast et al. |
| 6,487,343 B1 | 11/2002 | Lewandowski et al. |
| 6,512,940 B1 | 1/2003 | Brabec et al. |
| 6,522,915 B1 | 2/2003 | Ceballos et al. |
| 6,599,250 B2 | 7/2003 | Webb et al. |
| 6,615,064 B1 | 9/2003 | Aldrich |
| 6,622,046 B2 | 9/2003 | Fraley et al. |
| 6,667,803 B1 | 12/2003 | Flessland et al. |
| 6,682,135 B2 | 1/2004 | Zheng |
| 6,738,667 B2 | 5/2004 | Deno et al. |
| 6,839,583 B1 | 1/2005 | Lewandowski et al. |
| 6,839,592 B2 | 1/2005 | Grandjean |
| 6,850,787 B2 | 2/2005 | Weber et al. |
| 6,892,006 B2 | 5/2005 | Lewandowski et al. |
| 6,944,488 B2 | 9/2005 | Roberts |
| 6,997,879 B1 | 2/2006 | Turcott |
| 7,043,294 B1 | 5/2006 | Paris |
| 7,096,064 B2 * | 8/2006 | Deno et al. .................. 607/9 |
| 7,164,948 B2 | 1/2007 | Struble et al. |
| 7,165,893 B2 | 1/2007 | Schmitz |
| 7,177,686 B1 * | 2/2007 | Turcott .................. 607/23 |
| 7,239,385 B2 | 7/2007 | Schmitz et al. |
| 7,239,901 B2 | 7/2007 | Gritsenko |
| 7,277,757 B2 | 10/2007 | Casavant et al. |
| 7,302,294 B2 | 11/2007 | Kamath et al. |
| 7,809,441 B2 | 10/2010 | Kane et al. |
| 7,991,448 B2 | 8/2011 | Edgar, Jr. et al. |
| 8,038,626 B2 | 10/2011 | Cinbis et al. |
| 8,055,321 B2 | 11/2011 | Bernreuter |
| 8,090,432 B2 | 1/2012 | Cinbis et al. |
| 8,165,662 B2 | 4/2012 | Cinbis et al. |
| 2001/0047128 A1 * | 11/2001 | Benni .................. 600/323 |
| 2003/0004412 A1 | 1/2003 | Izatt et al. |
| 2003/0144584 A1 | 7/2003 | Mendelson |
| 2003/0187480 A1 | 10/2003 | KenKnight et al. |
| 2003/0199956 A1 | 10/2003 | Strubble |
| 2004/0024297 A1 | 2/2004 | Chen et al. |
| 2004/0220629 A1 | 11/2004 | Kamath et al. |
| 2005/0119586 A1 | 6/2005 | Coyle et al. |
| 2005/0148832 A1 | 7/2005 | Reghabi et al. |
| 2005/0277818 A1 | 12/2005 | Myers |
| 2006/0009685 A1 | 1/2006 | Finarov et al. |
| 2006/0106293 A1 | 5/2006 | Fantini |
| 2006/0253007 A1 | 11/2006 | Cheng et al. |
| 2007/0239052 A1 | 10/2007 | Bhunia |
| 2007/0239053 A1 | 10/2007 | Bhunia |
| 2007/0239215 A1 | 10/2007 | Bhunia et al. |
| 2007/0255148 A1 * | 11/2007 | Bhunia .................. 600/509 |
| 2008/0004513 A1 | 1/2008 | Walker et al. |
| 2008/0015424 A1 | 1/2008 | Bernreuter |
| 2008/0103538 A1 | 5/2008 | Walker et al. |
| 2008/0208020 A1 | 8/2008 | Cinbis |
| 2008/0208269 A1 | 8/2008 | Cinbis et al. |
| 2008/0306390 A1 | 12/2008 | Cinbis |
| 2010/0185252 A1 | 7/2010 | Björling et al. |
| 2010/0292548 A1 | 11/2010 | Baker, Jr. et al. |
| 2010/0317943 A1 | 12/2010 | Kuhn et al. |
| 2011/0066017 A1 | 3/2011 | Kuhn |

FOREIGN PATENT DOCUMENTS

| | | |
|---|---|---|
| EP | 1955653 | 8/2008 |
| GB | 1419701 | 12/1975 |
| WO | 9825669 | 6/1998 |
| WO | 03077750 | 9/2003 |
| WO | 2004091719 | 10/2004 |
| WO | 2007012931 | 2/2007 |
| WO | 2008105698 | 9/2008 |
| WO | 2008118042 | 10/2008 |
| WO | 2008151263 | 12/2008 |

OTHER PUBLICATIONS

Myers, Dean E., Noninvasive Method for Measuring Local Hemoglobin Oxygen Saturation in Tissue Using Wide Gap Second Derivative Near-Infrared Spectroscopy, Journal of Biomedical Optics 10(3), 034017 (May/Jun. 2005).

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305.

St Jude Medical, ME 317: Design for Manufacturability, Implantable Pulse Generator Optical Sensing System, Jun. 1, 2004, 225 pages.

M.N. Ericson et al., Development of an Implantable Oximetry-Based Organ Perfusion Sensor, Proceeding of the 26th Annual International Conference of the IEEE EMBS, Sep. 1-5, 2004, pp. 2235-2238.

JR Wilson et al., Noninvasive Detection of Skeletal Muscle Underperfusion with Near-Infrared Spectroscopy ion Patients with Heart Failure; Circulation: Journal of the American Heart Association, 1989;80; pp. 1668-1674.

* cited by examiner

TISSUE OXYGENATION MONITORING IN HEART FAILURE

RELATED APPLICATION

The present disclosure claims priority and other benefits from U.S. Provisional Patent Application Ser. No. 61/185,812, filed Jun. 10, 2009, entitled "TISSUE OXYGENATION MONITORING IN HEART FAILURE", incorporated herein by reference in its entirety.

REFERENCE TO RELATED APPLICATION

Cross-reference is hereby made to the commonly-assigned related U.S. Applications: U.S. application Ser. No. 12/797,736, U.S. application Ser. No. 12/797,744 and, U.S. application Ser. No. 12/797,770, all entitled "DEVICE AND METHOD FOR MONITORING ABSOLUTE OXYGEN SATURATION AND TOTAL HEMOGLOBIN CONCENTRATION", to Kuhn et al.; U.S. application Ser. No. 12/797,815 and, U.S. application Ser. No. 12/797,816, both entitled "TISSUE OXYGENATION MONITORING IN HEART FAILURE" to Cinbis et al.; U.S. application Ser. No. 12/797,831, now issued as U.S. Pat. No. 8,352,008, entitled "ACTIVE NOISE CANCELLATION IN AN OPTICAL SENSOR SIGNAL", to Kuhn et al.; U.S. application Ser. No. 12/797,781 and, U.S. application Ser. No. 12/797,793, now issued as U.S. Pat. No. 8,391,979, both entitled "SHOCK REDUCTION USING ABSOLUTE CALIBRATED TISSUE OXYGEN SATURATION AND TOTAL HEMOGLOBIN VOLUME FRACTION", to Kuhn et al.; and, corresponding to U.S. application Ser. No. 12/797,800 and, corresponding to U.S. application Ser. No. 12/797,811, now issued as U.S. Pat. No. 8,346,332, both entitled "ABSOLUTE CALIBRATED TISSUE OXYGEN SATURATION AND TOTAL HEMOGLOBIN VOLUME FRACTION", to Kuhn et al., all of which are incorporated herein by reference in their entireties.

TECHNICAL FIELD

The invention relates generally to medical devices and, in particular, to a medical device system and associated method for monitoring tissue oxygen availability in heart failure patients.

BACKGROUND

Implantable medical devices are available for monitoring and treating patients with heart failure. Such devices include physiological sensors for sensing signals correlated to physiological events or conditions. For example, implantable hemodynamic monitors may monitor blood pressure and heart rate. Pacemakers or implantable cardioverter/defibrillators (ICDs) are available that monitor a cardiac EGM/ECG signal and may provide heart failure therapies such as cardiac resynchronization therapy (CRT). CRT involves pacing one or more heart chambers to improve the synchronization of the heart chamber contractions and thereby improve the heart's ability to eject blood. However, not all patients respond to CRT. Currently, a challenge remains in prospectively identifying heart failure patients that will respond positively to CRT. As such, a heart failure patient may undergo implantation of a CRT device without significantly benefiting from the therapy.

Progression of heart failure leads to poor oxygenation of skeletal muscle tissue. A lack of cardiac reserve, i.e., the heart's inability to function above a basal level in response to an increased metabolic demand such as during exercise, can lead to tissue hypoxia during exercise. Poor tissue oxygenation and lack of cardiac reserve lead to exercise intolerance in heart failure patients. Many approaches to monitoring a heart failure patient involve monitoring blood pressure, heart wall motion, ejection fraction, heart rate and other hemodynamic measures. However, a need remains for sensing devices and methods for diagnostic, prognostic and therapy management purposes in heart failure patients.

DETAILED DESCRIPTION

Figure 1:
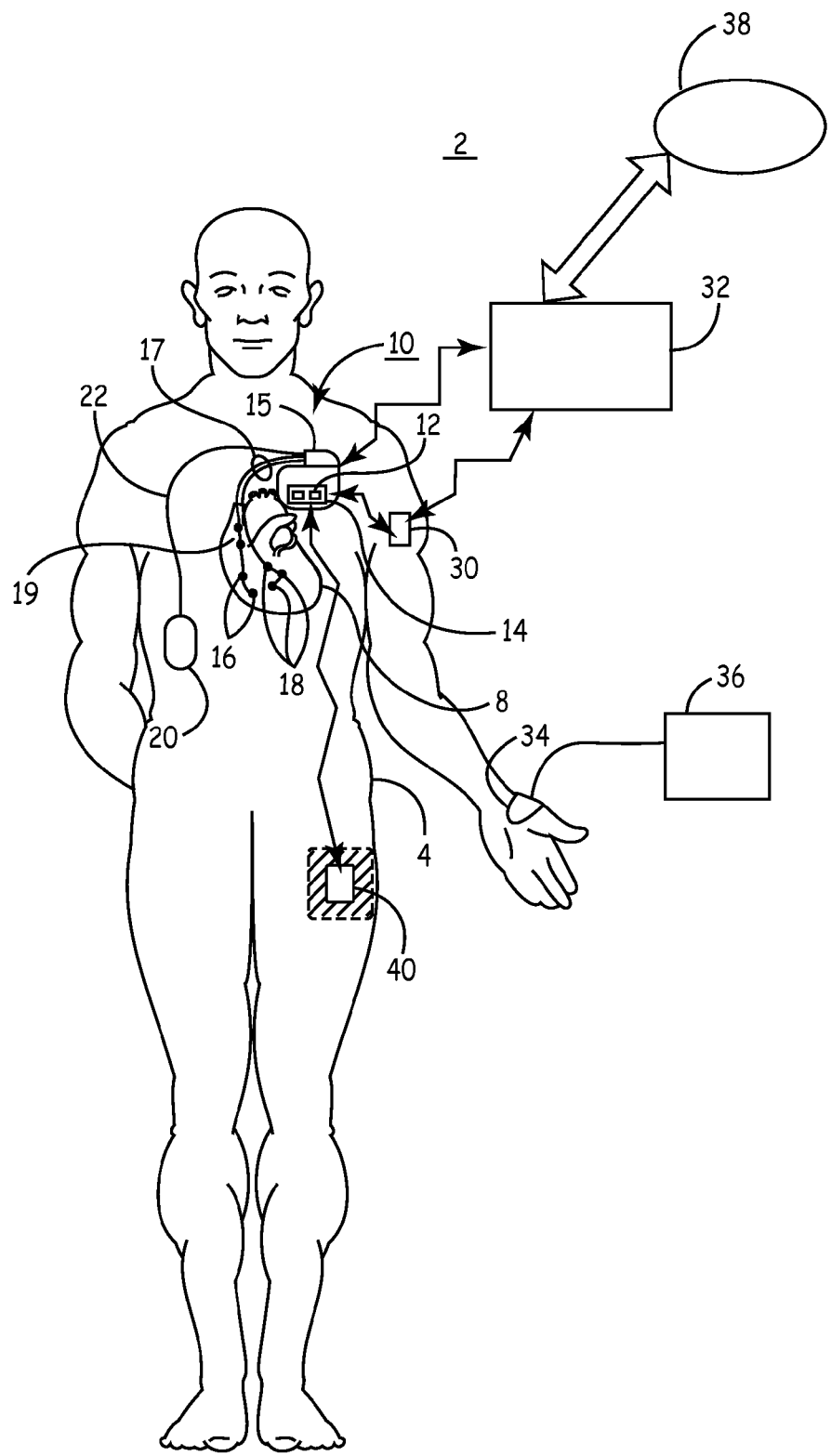
FIG. 1 is a schematic view of a medical device system for monitoring tissue oxygenation in a heart failure patient.

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In various embodiments described herein, an optical sensor is used to monitor tissue oxygenation in a measurement tissue volume. The measurement volume is the volume of tissue (including blood) in the optical path of the sensor. The term "tissue oxygenation" as used herein refers to the availability of oxygen to a localized tissue volume and thus refers generally to the availability of oxygenated hemoglobin. The term "total hemoglobin volume fraction" (HbT) refers to the concentration of red blood cells in a measurement volume carrying hemoglobin and thus relates to the total hemoglobin concentration as a fraction of a measurement volume. Stated differently, the total hemoglobin volume fraction, which can be expressed as a percentage, is the volume percentage of red blood cells carrying oxygenated and deoxygenated hemoglobin in the measurement volume. Thus a measurement of HbT will include contributions from red blood cells present in any arteries, capillaries, and veins which may be present in the measurement volume. Generally speaking, when the availability of oxygen to a body tissue is being monitored, the optical sensor is positioned such that the measurement volume extends through a relatively uniform tissue volume such that optical sensor signals used to compute measurements of tissue oxygenation correlate to the absolute tissue oxygen saturation ($O_2$Sat) and HbT in the microcirculation of the measurement volume.

Absolute tissue oxygen saturation is the portion (or percentage) of the total hemoglobin that is in an oxygenated state. More specifically, $O_2$Sat relates to the available hemoglobin binding sites holding an oxygen molecule. Thus, "tissue oxygenation monitoring" as used herein refers to monitoring both $O_2$Sat (or an index thereof) and HbT (or an index thereof). Tissue oxygenation monitoring may involve determining absolute measurements of $O_2$Sat and HbT, determining trends of these measurements, determining indices of oxygenation measurements or trends of indices. When either $O_2$Sat or HbT or measurements correlated thereto, are reduced, a blood-perfused tissue can become hypoxic.

The term "hypoxia" as used herein refers to a reduced availability of oxygen to the tissue. "Stagnant hypoxia" occurs when inadequate blood flow fails to transport sufficient oxygen to the tissue, such as in heart failure. As such, stagnant hypoxia generally occurs when tissue perfusion is low, e.g., due to low cardiac output.

The status of a heart failure patient may be monitored by assessing the oxygen available to tissue through monitoring absolute tissue $O_2$Sat and HbT. Generally speaking, as heart failure worsens, tissue oxygenation can worsen. As heart failure improves, for example in response to a heart failure therapy, tissue oxygenation will improve. In particular, a heart failure patient's cardiac reserve is often diminished, reducing the ability of the heart to respond to an increased metabolic demand by increasing cardiac output. As a result, the tissue oxygen availability does not increase to meet an increased metabolic demand due to exercise. As such, tissue oxygenation during exercise may be lower in a heart failure patient as compared to a patient having normal cardiac function performing the same level of exercise.

As will be described herein, tissue oxygenation monitoring applications may include chronic or acute monitoring of tissue oxygenation using an implantable or external medical device including an optical sensor. As used herein, "chronic" monitoring generally refers to monitoring a tissue for more than one day using continuous or periodic measurements while "acute" monitoring generally refers to monitoring a tissue for one day or less, for example, testing performed during a clinical visit or measurements performed during a surgical procedure.

FIG. 1 is a schematic view of a medical device system 2 for monitoring tissue oxygenation in a heart failure patient. Medical device system 2 includes an implantable medical device (IMD) 10 provided for delivering a heart failure therapy, which may be a cardiac stimulation therapy, a nerve stimulation therapy, or a drug or biological agent.

System 2 may alternatively or additionally include a cardiac assist device which aids or replaces the blood pumping function of the heart. Examples of cardiac assist devices include intra-aortic balloon pumps, left ventricular assist devices (LVAD), total artificial heart (TAH) or other blood pumps. As will be described herein, an optical sensor may be used with any of these therapy delivery devices to monitor tissue oxygenation to measure the effectiveness of the therapy and possibly to optimize their settings.

Alternatively, medical device system 2 may be provided for monitoring a patient without including therapy delivery capabilities. As such, IMD 10 may be embodied as any of a number of implantable medical devices, including pacemakers, implantable cardioverter defibrillators (ICDs), nerve stimulators, fluid delivery pumps, hemodynamic monitors, ECG monitors, or the like.

In one embodiment, IMD 10 includes an optical sensor 12 incorporated in hermetically-sealed housing 14 of IMD 10. Housing 14 encloses an IMD battery and other device circuitry and components needed for performing device functions. Housing 14 includes at least one opening or window through which light is emitted from a light emitting portion of the optical sensor 12 and at least one additional window through which light is detected by a light detecting portion of optical sensor 12.

It is recognized that sensor 12, and any of the other sensor embodiments described herein, may include multiple light emitting and/or light detecting portions to allow different combinations of emitting and detection portions to be selected for performing oxygenation measurements, which may include using emitting and detecting portions at different distances apart. The distance between the emitting and detecting portions determines, in part, the optical pathway of the sensor and thus the measurement volume and depth. Therefore, selection of different emitting and detecting portions and different emitting-to-detecting spacings allows oxygenation measurements to be performed in different measurement volumes in tissue adjacent to the sensor 12.

In some embodiments, an optical sensor 20 may be carried by a lead 22 extending from IMD 10. Lead 22 is coupled to circuitry within housing 14 via a connector block 15 including appropriate electrical connections and feedthroughs to allow circuitry within housing 14 to be coupled to sensor 20. A lead-based sensor 20 may be used to deploy sensor 20 at a tissue site remote from the implant site of IMD 10. Lead 22 may be tunneled extravascularly, e.g., subcutaneously or submuscularly, to a desired monitoring site.

In alternative embodiments, a lead 22 carrying a sensor 20, e.g. at a distal end of the lead 22, may be advanced within the vascular system and remain within a blood vessel 25 for measuring $O_2$Sat and HbT in tissue adjacent to the blood vessel. Alternatively, lead 24 may be advanced intravascularly to a desired tissue site then advanced through the vessel wall, for example by puncturing the vessel wall, for placement at an adjacent tissue site.

System 2 may additionally or alternatively include an optical sensor 30 embodied as an implantable wireless optical sensor housed in a hermetically sealed housing. Sensor 30 includes a power supply and circuitry for performing tissue oxygenation measurements and further includes a telemetry module (not explicitly shown) enabling sensor 30 for wireless communication with IMD 10 or an external medical device 32. External medical device 32 may be a bedside monitor, a patient home monitor or a device programmer used to program IMD 10 or sensor 30.

A wireless sensor 30 may be implanted at a desired monitoring site remote from IMD 10 without the surgical constraints imposed by tethering sensor 30 to IMD 10 using a conductive lead. Wireless sensor 30 is shown implanted in an upper limb of patient 4, however a wireless sensor 30 may be positioned along any peripheral or core body site for monitoring a desired tissue volume. A wireless sensor 30 may be implanted for monitoring purposes only, without therapy delivery capabilities, and may be used alone or in conjunction with another IMD 10 for monitoring tissue oxygenation in patient 4.

System 2 may include an external, wireless optical sensor 40 for ambulatory, chronic or acute monitoring of tissue oxygenation. Sensor 40 emits light through the skin of the patient to obtain light attenuation measurements associated with the absorption of light by a tissue volume. External wireless optical sensor 40 is shown positioned along a lower limb of patient 4 but may be positioned along any peripheral or core body location for monitoring tissue oxygenation in a desired tissue volume. External sensor 40 may be held in a stable position using an adhesive patch or tape or using a securable band or cuff. External wireless optical sensor 40 includes a power supply and circuitry for performing tissue oxygenation measurements and telemetry circuitry enabling wireless communication between sensor 40 and IMD 10 and/or an external medical device 32.

IMD system 2 may include an external sensor 34 in wired communication with a monitor 36 for performing tissue oxygenation measurements transcutaneously. External sensor 34 and monitor 36 may be used in a patient's home, in a clinic, or in a surgical theater for monitoring tissue oxygenation for periodic patient monitoring or during implantation of IMD 10 or sensor 30.

The sensors described herein relate generally to a "reflection" mode of operation wherein the light emitting and light detecting portions of the sensor are in a substantially side-by-side arrangement and detected light is scattered by the tissue back to the detection portion. It is contemplated that an optical sensor may be configured to operate in a "transmission" mode wherein the light emitting and light detecting portions of the sensor are arranged in facing opposition to each other. Detected light is light that is transmitted through the tissue. Furthermore, it is contemplated that in transmission mode configurations, one of the light emitting portion and the light detecting portion can be positioned externally against the skin "looking in" and the other can be positioned subcutaneously or submuscularly, "looking out" in facing opposition with the external portion.

As will be further described below, a medical device system 2 including an optical sensor for monitoring tissue oxygenation will include a processor for computing tissue oxygenation measurements. In one embodiment, absolute $O_2Sat$ and HbT measurements are computed from a light detector output signal. In other embodiments, non-calibrated tissue oxygenation measurements may be computed. A processor and other signal conditioning circuitry for computing oxygenation measurements from raw signals may be included in or distributed across any of the components shown in system 2, including external device 32, IMD 10, wireless sensors 30 and 40, lead-based sensor 20, or monitor 36.

External device 32 is shown in communication with a networked patient monitoring database 38. Tissue oxygenation data may be transmitted to a monitoring database 38 to allow a clinician to monitor patient 4 remotely using a centralized Internet website or networked computer system. An example of a remote patient management system in which tissue oxygenation monitoring may be incorporated for managing heart failure patients is generally described in U.S. Pat. No. 6,599,250 (Webb, et al.), hereby incorporated herein by reference in its entirety.

In various embodiments, IMD 10 is provided for delivering a heart failure therapy. IMD 10 is shown coupled to cardiac leads 17 which may be transvenous leads used to deploy electrodes 16 and 18 in one or more chambers of the patient's heart 8. For example, leads 17 may include a right ventricular lead and a coronary sinus lead. A right ventricular lead is advanced transvenously into the right ventricle to position electrodes 16 for right ventricular sensing and stimulation. Electrodes 19 positioned in the right atrium may be carried by a right ventricular lead as shown or by a separate lead. A coronary sinus lead is advanced further through the right ventricle into the coronary sinus and a cardiac vein to position electrodes 18 for sensing and stimulation in the left ventricle. Additional leads and/or electrodes may be included for sensing and stimulating in the atrial chambers or for delivering high-voltage cardioversion/defibrillation shock pulses.

Leads 17 and electrodes 16 and 18 may be used to deliver cardiac resynchronization therapy (CRT) for treating heart failure. An example of a device and method for delivering CRT is generally described in U.S. Pat. No. 6,839,592 (Grandjean), hereby incorporated herein by reference in its entirety. Other stimulation therapies that may be delivered in a heart failure patient include anti-tachycardia pacing therapies, minimum ventricular pacing, and rate-responsive pacing.

IMD 10 may alternatively be coupled to a lead provided for delivering stimulation to a nerve, e.g. the vagus nerve, for treating heart failure. System 2 may additionally or alternatively include leads or catheters extending from IMD 10 for delivering a fluid, e.g. a cardiac drug or biological agent, administered to treat heart failure.

IMD 10 may be in wireless communication with external monitor 36 to enable cooperative operation for obtaining tissue oxygenation measurements before and during delivery of a heart failure therapy. Alternatively, external device 32 may be in wireless communication with IMD 10 and in wired or wireless communication with monitor 36 to allow IMD 10, external monitor 36, and external device 32 to operate cooperatively to obtain tissue oxygenation measurements before and during delivery of a heart failure therapy. It is recognized, that the functionality of external device 32 and monitor 36 may be combined in a single unit.

Figure 2:
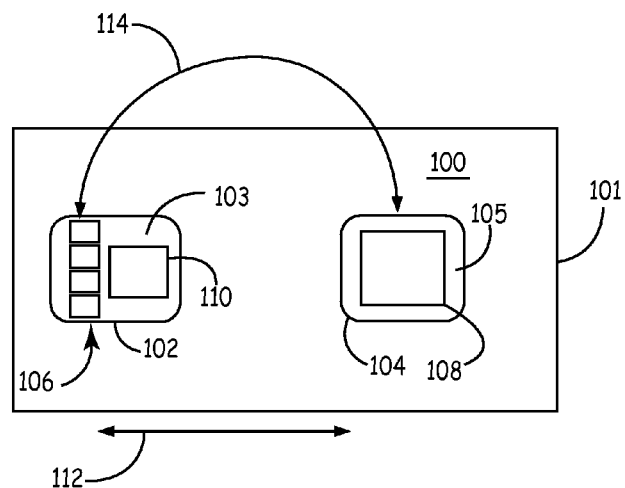
FIG. 2 is a top, schematic view of an optical sensor according to one embodiment.

FIG. 2 is a top, schematic view of an optical sensor according to one embodiment. It is recognized that numerous optical sensor configurations may be used for monitoring tissue oxygenation, and the methods and devices described herein are not limited to a particular optical sensor configuration. In general, any optical sensor that acquires measurements of the attenuation of light scattered by or transmitted through a tissue volume for computing a measurement correlated to tissue oxygenation may be used. In some embodiments, tissue oxygenation measurements may include a non-calibrated index of oxygen saturation determined using a two-wavelength optical sensor, typically emitting and detecting red and infrared light, as generally disclosed in U.S. Patent Application No. 2007/0255148 (Bhunia), hereby incorporated herein by reference in its entirety. In other embodiments, tissue oxygenation measurements may include non-calibrated indices of oxygen saturation and blood volume determined using a two-wavelength (typically red and infrared) optical sensor or a three-wavelength (typically red, isosbestic and infrared) optical sensor as generally described in U.S. Patent Publication No. 2008/0208269 (Cinbis, et al), hereby incorporated herein by reference in its entirety.

In the illustrative embodiments described herein, calibrated measures of $O_2Sat$ and HbT are measured using a four wavelength optical sensor. Examples of optical sensors emitting and detecting at least four wavelengths are generally described in U.S. Pat. Appl. Ser. No. 61/185,818, hereby incorporated herein by reference in its entirety. Second derivatives of attenuation spectra can be used to obtain a calibrated, volume-independent measurement $O_2Sat$ and a calibrated measurement of HbT. Determination of absolute calibrated measures of $O_2Sat$ and HbT allows tissue oxygenation at a particular time point to be evaluated as well as long term changes in tissue oxygenation (e.g. over hours, days or weeks) to be monitored. The use of non-calibrated indices of tissue oxygen saturation and blood volume available from 2- or 3-wavelength optical sensor devices allows short term trends in tissue oxygenation (for example over seconds or minutes) to be monitored. Both short-term monitoring of tissue oxygenation index trends and absolute value and long-term monitoring of absolute calibrated measurements of tissue oxygenation can be useful in monitoring a heart failure patient and managing a heart failure therapy.

While the illustrative embodiments described herein rely on 4-wavelengths (or more) of light attenuation measurements to obtain calibrated measurements of tissue oxygenation, it is recognized that uncalibrated indices of tissue oxygenation measurements obtained from 2- or 3-wavelength optical sensor devices may be substituted, particularly when short-term trends are being evaluated for assessing tissue oxygenation in a heart failure patient. For example, a short-term trend in tissue oxygenation measured from immediately before initiating a heart failure therapy and subsequent to delivery the heart failure therapy, e.g. within the first minute, may be evaluated using 2-, 3- or 4- or more wavelength optical sensor devices.

Sensor 100 may generally correspond to sensor 12, 20, 30, 34 or 40 in FIG. 1. Sensor 100 includes a light emitting portion 102 and a light detecting portion 104. Light emitting portion 102 includes one or more light sources 106 positioned to emit light through a lens 103 sealed in an opening in hermetically-sealed housing 101. Light source(s) 106 may be embodied as single white light source or multiple light sources emitting light at separate spaced-apart wavelengths. Suitable light sources include, without limitation, optoelectronic devices such as light emitting diodes (LEDs), lasers such as vertical cavity surface emitting lasers (VCSELs), luminescent or phosphorescent and incandescent light sources. In one embodiment, light sources 106 are embodied as light emitting diodes (LEDs) emitting light in the visible, e.g. red, and/or infrared light spectrum.

For example, light sources 106 may include four LEDs in emitting portion 102 for emitting light at separate wavelengths of 680 nm, 720 nm, 760 nm, and 800 nm. Alternatively, four LEDs provided as light sources 106 may emit light at 660 nm, 720 nm, 760 nm, and 810 nm. In another embodiment, four LEDs are included emitting light at 720 nm, 760 nm, 810 nm, and 850 nm. In yet another embodiment, four LEDs are included that emit light at 720 nm, 760 nm, 810 nm, and 890 nm. Any combination of light sources emitting light at any of the wavelengths mentioned herein may be used. Furthermore, it is recognized that the specified wavelengths are approximate and each light source may emit a narrow band of light wavelengths which is approximately centered on, or at least includes, the specified wavelength. The light sources may be controlled to emit light sequentially or simultaneously.

In the embodiment shown, the light emitting portion 102 further includes a reference light detector 110, which may be embodied, for example, as a photodiode. The light entering an adjacent tissue volume from emitting portion 102 may change over time during chronic use of sensor 100 due, for example, to drift in the photonic output of light source(s) 106 and/or changes in the optical properties of the materials encountered by light emitted by light sources 106 before entering an adjacent tissue volume, e.g. lens 103. Reference light detector 110 provides an output signal for measuring or detecting changes in the intensity of the light emitted by emitting portion 102.

The reference light detector 110 output signal can be used in computing or adjusting $O_2$Sat and HbT measurements. Additionally or alternatively, an output signal from reference light detector 110 can be used as a feedback signal for controlling the drive signals applied to light sources 106 to cause light emission.

In other embodiments, a light detector 110 is not included in the emitting portion 102. The emitted light intensity is assumed to be stable throughout the usable life of the sensor so as not to introduce significant error in light attenuation measurements used for computing tissue $O_2$Sat and HbT.

The light detecting portion 104 includes a light detector 108 positioned to receive light through a lens 105 mounted in an opening in housing 101. The light detector 108 may be embodied as a photodiode. Other components suitable for use as a light detector include a photoresistor, phototransistor, photovoltaic cell, photomultiplier tube, bolometer, charge-coupled device (CCD) or an LED reverse-biased to function as a photodiode. Light detector 108 receives light scattered by an adjacent tissue volume. The distance 112 between the light sources 106 and the light detector 108 will influence the optical path 114 (shown schematically) of sensor 100. Greater spacing (longer distance 112) between the emitting and detecting portions will result in a longer optical pathway 114, extending deeper in the adjacent tissue volume, than relatively shorter spacing between light sources 106 and light detector 108. As such, different spacing between emitting and detecting portions 102 and 104 will result in tissue oxygenation measurements relating to different depths of an adjacent body tissue.

Figure 3:
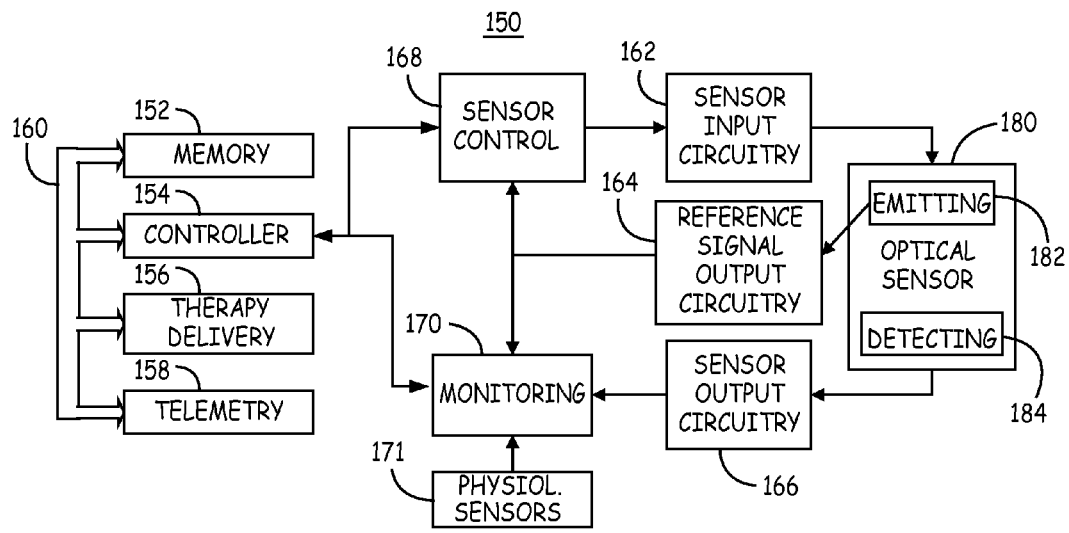
FIG. 3 is a functional block diagram of a medical device system including an optical sensor for monitoring tissue oxygenation.

FIG. 3 is a functional block diagram of a medical device system 150 including an optical sensor 180 for monitoring tissue oxygenation. The functionality described in conjunction with FIG. 3 may be implemented in or distributed across any of the medical device system components shown in FIG. 1. For example, the functional blocks shown in FIG. 1 may be implemented in IMD 10, an implantable lead-based sensor 20, an implantable wireless sensor 30, an external wireless sensor 40, an external wired sensor 40, an external device 32, an external monitor 36, or any combination thereof (all shown in FIG. 1).

Device system 150 includes an optical sensor 180, which may be incorporated along a hermetically sealed housing of a device or carried by a lead. Medical device system 150 further includes sensor input circuitry 162, sensor output circuitry 166, and optionally includes reference signal output circuitry 164 when a reference light detector is included in the optical sensor 180 for measuring the intensity of emitted light.

Optical sensor 180 generally includes a light source for emitting light through a blood perfused tissue of the patient and a light detector for generating a signal representative of an intensity of light emitted and scattered by the blood perfused tissue to the light detector. The light passed through the tissue (including blood) may be selected to include four or more wavelengths for use in computing a volume-independent measure of $O_2$Sat, from which an absolute, calibrated tissue $O_2$Sat may be derived. Typically, the intensity of scattered light falling in the red part of the visible light spectrum and the infrared (IR) portion of the light spectrum is measured.

Absorption of light in the red to infrared spectrum by blood-perfused tissue will vary depending on the presence of chromophores (for example hemoglobin and/or myoglobin) in oxygenated and deoxygenated states present in the measurement volume. The light scattered by blood-perfused tissue and received by the light detector can therefore be used to measure attenuation of light emitted by the sensor due to light absorption which will be correlated to the oxygen available ($O_2$Sat and HbT) to the tissue. (The measured light attenuation may not be a precise measurement of the actual light absorption by the tissue volume since light reflections and scattering not detected by the sensor may cause attenuation of the remitted light intensity not attributed to actual light absorption by the tissue.) Processing of the optical sensor output signal thus allows tissue oxygen availability to be measured. Tissue oxygenation is used, in turn, for monitoring a patient's heart failure condition or a response to a heart failure therapy.

Sensor input circuitry 162 is coupled to a light emitting portion 182 of optical sensor 180. Light emitting portion 182 includes one or more light sources for emitting light that includes at least four different wavelengths for computing calibrated tissue oxygenation measurements. In alternative embodiments, sensor 180 may be two-wavelength or three-wavelength sensor used for computing non-calibrated measures of tissue oxygenation. Light sources may emit light at discrete, spaced-apart wavelengths or a single white light source may be used. The measurement of light attenuation for at least four different wavelengths allows a calibrated absolute $O_2$Sat measurement to be obtained as will be described herein. Sensor input circuitry 162 provides input signals to the optical sensor 180. In particular, sensor input circuitry 162 provides the drive signals applied to the light source(s) included in light emitting portion 182 to cause controlled light emission, e.g. controlled intensity, time duration and frequency.

Sensor input circuitry 162 is controlled by sensor control module 168 which coordinates the beginning time, duration, and frequency of drive signals produced by sensor input circuitry 162. Control signals may include a period of no light emission for ambient light measurement. Drive signals may be applied to individual light sources simultaneously to cause "mixed" light emission from all light sources.

In one embodiment, the drive signals are applied sequentially to cause sequential (i.e., non-simultaneous) light emission by individual light sources emitting light at spaced apart wavelengths. In this way, a light detecting portion 184 of sensor 180 will receive scattered light at an individual wavelength at any given time during the operation of sensor 180. It is recognized that referring to an "individual" or "one" wavelength can include a narrow bandwidth of wavelengths approximately centered on, or at least including, the specified individual wavelength emitted by a light source.

The sequential emission of light wavelengths allows multiple light signals to be sequentially measured for each wavelength. A single $O_2$Sat or HbT measurement will require some minimum interval of time corresponding to the cumulative time durations of each of the separately emitted wavelengths. The time-based sequencing of emitted light may include an interval of no light emission to allow for ambient light measurements and correction of the measured light signals for the presence of ambient light during light emission by the sensor.

In alternative embodiments, the sensor input circuitry 162 is controlled by sensor control module 168 to deliver drive signals simultaneously to each of the light sources at separate, unique frequencies. For example, light sources may be controlled to emit light simultaneously with each individual wavelength having a signature frequency fluctuation. The detecting portion 184 will receive scattered light at all of the wavelengths corresponding to the individual wavelengths simultaneously with each wavelength modulated to a signature frequency. A light detector signal is then demodulated to obtain the individual wavelength signals.

This frequency multiplexing method of controlling the light emitting portion 182 allows simultaneous light emission and detection such that changes in light attenuation by the tissue due to oxygen and hemoglobin changes in the measurement volume can be measured simultaneously for all of the wavelengths rather than at discrete time intervals. This allows for a more instantaneous measurement of $O_2$Sat and HbT as compared to the sequentially-acquired signals for separate wavelengths in the time-multiplexed method of controlling light emission.

The different wavelengths may be modulated at frequencies that are much greater than the frequency of ambient light changes. Demodulation of the detected light signal will reduce or eliminate effects of ambient light artifact since low frequency components of the detected light signal corresponding to ambient light changes will be substantially removed from the demodulated light detector output signal.

Sensor output circuitry 166 receives the light detector signal from light detecting portion 184 and demodulates, digitizes, filters or performs other appropriate signal conditioning to provide a digital output signal to monitoring module 170. Sensor output circuitry 166 may include an analog-to-digital converter and memory for digitizing an analog output signal from detecting portion 184, providing the digitized signal to monitoring module 170, storing measurement results for future retrieval as well as storing calibration coefficients.

In one embodiment, monitoring module 170 includes processing circuitry that uses the optical signal to compute a volume-independent measurement of $O_2$Sat and a measurement of HbT (which is both oxygen and volume dependent) using the intensities of the multiple wavelengths measured by detecting portion 184.

As used herein, a "volume-independent" measure of oxygen saturation refers to a measurement that is substantially independent of the size of the optical sensor path that encompasses a measurement volume within a substantially uniform tissue. In other words, in a uniform, homogenous tissue, a longer optical pathway that encompasses a larger measurement volume and a relatively shorter optical pathway that encompasses a smaller measurement volume within the same uniform tissue will produce substantially equal $O_2$Sat measurements. A volume-dependent measure of oxygen saturation would be dependent on oxygen and the measurement volume and would thus produce two different measurements for two different measurement volumes in the same uniform, homogenous tissue. The second derivative method for computing $O_2$Sat as described herein eliminates scattering effects of a changing measurement volume and provides a volume-independent measurement of $O_2$Sat.

A homogenous tissue is a tissue that includes structures that are relatively small compared to the measurement volume. For example, if measurement volume is related to emitting-to-detecting spacing, a homogenous tissue might be a tissue wherein tissue structures or features have a dimension of approximately 1/10 of the emitting-to-detecting spacing or less. A uniform tissue is a tissue that has uniform oxygenation through the depth of the measurement volume in contrast to an oxygenation gradient. If a tissue is non-uniform or non-homogeneous, different oxygen saturation measurements will be obtained depending on the optical path of the sensor.

In some embodiments, a calibrated, absolute $O_2$Sat and calibrated HbT are derived from the light detector output signal and provided to a device controller 154 (which may include a processor, state machine or other control circuitry) for monitoring tissue oxygenation and controlling device-delivered therapy. In particular, the $O_2$Sat and HbT measurements may be used to detect a change in a patient's heart failure condition.

System 150 includes a therapy delivery module 156. The monitored $O_2$Sat and HbT may be used in determining when a therapy is needed and in controlling therapy delivery. Therapy delivery module 156 may include electrical pulse generation capabilities for delivering cardiac pacing pulses, cardioversion/defibrillation shocks, or nerve stimulation therapies. Therapy delivery module 156 may additionally or alternatively include a fluid delivery pump for delivering a pharmaceutical or biological fluid to the patient, such as cardiac drugs or other therapeutic fluids. In one embodiment, therapy delivery module 156 is coupled to cardiac electrodes for delivering cardiac resynchronization therapy (CRT) for delivering pacing pulses to two or more heart chambers.

Device 150 may include other sensors 171 for sensing physiological signals such as ECG or cardiac EGM signals, blood pressure, patient activity, patient posture, heart sounds, temperature, or the like. Such sensor signals may be used in combination with the monitored $O_2$Sat and HbT (or tissue oxygenation indices) for detecting a patient condition. Other physiological sensors may also be used in triggering the acquisition of tissue oxygenation measurements, adjusting thresholds for detecting insufficient oxygen availability, and establishing different baseline measurements for different patient conditions (e.g., different activity levels, different patient postures, etc.).

In one embodiment, an activity sensor is included to provide a signal corresponding to activity of the patient as an indicator of metabolic demand. An activity sensor signal can be used to compute a sensor-indicated rate (SIR) for use in rate-responsive pacing. An activity sensor signal may be used in combination with tissue oxygenation measurements to determine if a heart failure therapy, such as CRT, needs to be adjusted for improving tissue oxygen availability during periods of exercise.

Data acquired by processor 154 relating to tissue oxygenation measurements may be stored in memory 152 and/or transferred to a medical device programmer, home monitor, computer, or other external or bedside medical device via wireless telemetry module 158 for display and/or review by a clinician. Data relating to tissue oxygenation may also be transmitted to another implantable or external medical device for use in controlling a device delivered therapy. Processor 154 transmits data to and from memory 152, therapy delivery module 156, and telemetry module 158 via data/address bus 160.

As described above, some embodiments include a reference light detector in the light emitting portion 182 of sensor 180. Reference signal output circuitry 164 may then be included for receiving a light detection signal from the reference light detector and providing a reference output signal to sensor control 168 and/or to monitoring module 170. In one embodiment, the reference signal output circuitry provides an emitted light intensity feedback signal to sensor control 168 in a feedback control loop to maintain emitted light at each wavelength at desired relative intensities. Drive signals applied to a light source in light emitting portion 182 can be automatically adjusted to maintain the emitted light within a desired intensity range for each wavelength measured by the detecting portion 184. In this way, the emitted light spectra is reliably maintained over time promoting the accuracy of $O_2$Sat and HbT measurements computed using stored calibration constants or assuming stable light emission intensity. Accordingly sensor control 168 may include comparators, analog-to-digital convertors, and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each desired wavelength. The attenuation at each wavelength is used to compute second derivative attenuation spectra as will be described in greater detail below which enables derivation of a volume-independent measure of $O_2$Sat.

Alternatively, monitoring module 170 uses changes in the emitted light intensity to adjust a computed $O_2$Sat. $O_2$Sat may be computed assuming a stable emitted light intensity. The actual emitted light intensity may be measured and used to adjust a computed $O_2$Sat. For example, an initially measured emitted signal intensity and a currently measured emitted signal intensity can be used to adjust or correct an absolute $O_2$Sat and HbT computed using only the light detector signal from detecting portion 184 and calibration constants.

Figure 4:
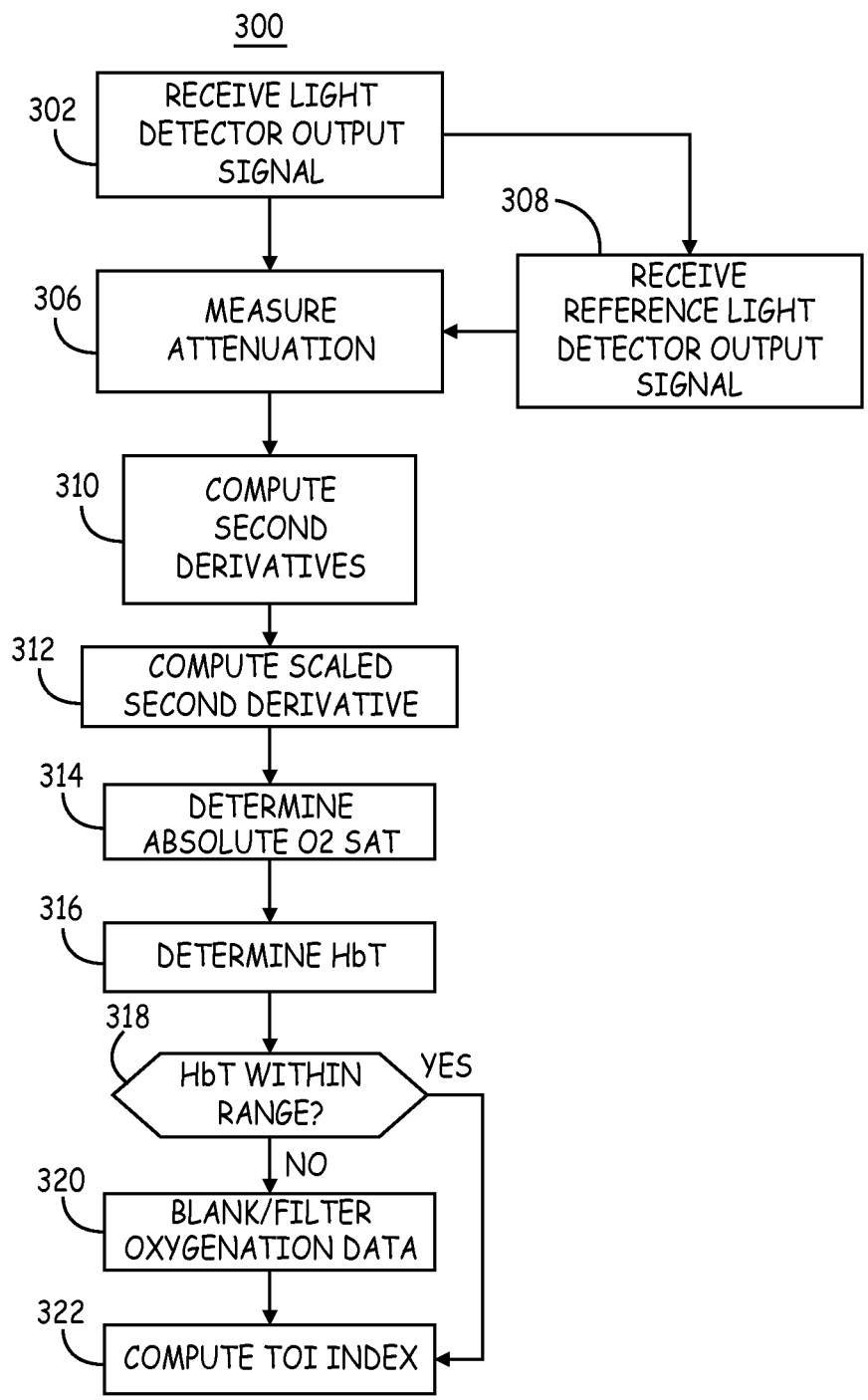
FIG. 4 is a flow chart of a method for operating an optical sensor during tissue oxygenation monitoring.

FIG. 4 is a flow chart of a method 300 for operating an optical sensor during tissue oxygenation monitoring. Flow chart 300 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 302, the optical sensor is controlled to emit light and the light detector output signal is received from the light detecting portion of the sensor. The light detector output signal may be filtered and corrected for ambient light and baseline offset. If a reference light detector is included in the light emitting portion, the reference light detector may provide an output signal for measuring the light intensity emitted by the sensor at block 308.

At block 306, the attenuation spectrum is measured. In one embodiment, the attenuation of four wavelengths in the red to infrared spectrum is measured. The attenuation of the four different wavelengths may be measured using sequential detection of the different wavelengths by the light detector when a time multiplexed light emission control algorithm is used. Alternatively, measurement of the four different wavelengths may involve demodulation of simultaneously detected light at the four different wavelengths when frequency multiplexed light emission is used. In other embodiments, remitted light from a white light source (or simultaneously emitting separate light sources) may be filtered to obtain the four different wavelength attenuation signals. Remitted light is the light that is scattered by the adjacent tissue volume and received by the light detecting portion (or reference light detector) of the optical sensor. The attenuation of remitted light for a given wavelength ($\lambda$) can be measured as the negative logarithm of the ratio of the emitted light intensity ($i_{in}$) to the remitted light intensity ($i_{out}$):

$$A(\lambda) = -\log(i_{in}/i_{out})_\lambda \qquad (1)$$

wherein $i_{in}$ can be measured using the output signal of a reference light detector in the light emitting portion of the sensor, and $i_{out}$ is measured using the output signal of the light detecting portion for a given wavelength. The term "attenuation" measurement as used herein generally refers to a measure of the attenuation of light due to absorption and scattering by tissue along the optical path of the sensor. The measured attenuation may therefore not be an exact measurement of the actual light absorption by the tissue volume since light reflections and scattering may cause attenuation of the remitted light intensity not attributed to actual light absorption by the tissue.

In some embodiments, the emitted intensity for each wavelength $i_{in}$ is assumed constant and is optionally measured prior to implantation, e.g., at the time of manufacture, and assumed to be sufficiently stable throughout the usable life of the sensor and not cause significant measurement error. In this case, a reference light detector may be eliminated from the light emitting portion of the sensor and thereby reduce overall size and complexity of the sensor. One method for measuring the emitted intensity prior to implantation uses the light detecting portion to measure the remitted light when the sensor is positioned within a calibrated reflective housing. The construction of the emitting portion is designed to minimize or prevent drift in the emitted light intensity over time. Design considerations include minimizing the distance between the tissue and the photonic surfaces of the light source(s).

The attenuation for four wavelengths is determined to allow the second derivative with respect to wavelength of the attenuation spectra at two intermediate wavelengths to be computed. This determination of second derivatives at two intermediate wavelengths allows for computation of a scaled second derivative. By properly selecting the intermediate wavelengths, a scaled second derivative is an oxygen-dependent and volume-independent ratio and therefore provides a measure of $O_2$Sat. At block 310, the attenuation measurement for two wavelengths intermediate the four detected wavelengths is converted to a second derivative (D″), expressed generally as:

$$D''(\lambda_i) = A(\lambda_{i+1}) - 2A(\lambda_i) + A(\lambda_{i-1}) \quad (2)$$

wherein $A(\lambda_i)$ is the light attenuation, measured according to Equation 1 above, at the wavelength for which the second derivative is being computed, $A(\lambda_{i+1})$ is the attenuation at the next higher wavelength and $A(\lambda_{i-1})$ is the attenuation at the next lower wavelength of the four wavelengths. Equation 2 assumes equal spacings between the four wavelengths. When unequal spacings are used, a different equation for the second derivative with respect to wavelength is required to account for the different wavelength spacings by retaining the differences between wavelengths in denominators of the first and second derivative equations.

The second derivative of a selected intermediate wavelength is scaled by another computed second derivative at block 312. In one embodiment, the attenuation is measured for wavelengths at 680 nm, 720 nm, 760 nm, and 800 nm. The second derivatives of the attenuation spectra are computed at 720 nm and 760 nm and the second derivative at 720 nm is scaled by the second derivative at 760 nm. The scaled second derivative (SD″) of the 720 nm attenuation can be expressed as $$SD'' = D''(720)/D''(760) \quad (3)$$

This SD″(720) is dependent on oxygen saturation of the hemoglobin present in the measurement volume but independent of the size of the measurement volume, defined by the optical path of the sensor (assuming a uniform, homogenous tissue). Thus, SD″(720) is independent of the total hemoglobin present in the measurement volume and independent of the optical path length. The reduced dependence on total hemoglobin and optical path length is expected to reduce the effects of motion artifact on a measurement of $O_2$Sat based on SD″(720). Thus, measuring attenuation for at least four wavelengths allows the second derivatives of two intermediate wavelengths to be computed, allowing computation of a measurement volume-independent, scaled second derivative.

The optical sensor may be calibrated at the time of device manufacture using control samples, for example in an in vitro blood circuit, having known oxygen saturation and total hemoglobin concentration. The calibration process generate a look-up table relating second derivatives computed from the light detector output signal and the known $O_2$Sat and HbT. The look-up table is stored in the device memory. The look-up table can then be used to derive absolute calibrated $O_2$Sat and Hbt values from an optical sensor measurement.

Alternatively, calibration methods may include curve-fitting methods to solve for coefficients defining best-fit curves to the calibration data. In one embodiment, the absolute tissue oxygen saturation is defined by:

$$O_2 sat = A e^{B(SD''(\lambda_i))} + C \quad (4)$$

wherein SD″ is a scaled second derivative of the attenuation spectra at a selected intermediate wavelength ($\lambda_i$) emitted and detected by the optical sensor. As described above, a scaled second derivative of the attenuation spectra at a selected wavelength is determined by the monitoring module using the light detector signal. The scaled second derivative is the ratio of the second derivative with respect to wavelength of the attenuation spectra at a selected wavelength $\lambda_i$ to the second derivative of the attenuation spectra at another selected wavelength used for scaling. By properly selecting the wavelength $\lambda_i$ and the other wavelength used for scaling, the scaled second derivative is an oxygen-dependent and volume-independent ratio. The coefficients A, B and C are determined through best-fit analysis of measurements of the scaled second derivative for calibration samples having known oxygen saturation.

The total tissue hemoglobin volume fraction can be defined by the equation:

$$HbT = [M(100 - O_2 Sat)^N + L] * [(D''(\lambda i) / SF] \quad (5)$$

wherein M, N, and L are coefficients determined during calibration and D″(λi) is the second derivative of the attenuation spectra with respect to wavelength at the selected intermediate wavelength $\lambda_i$. D″(λ) is measured for samples containing known total hemoglobin volume fraction and known oxygen saturation. The calibration coefficients M, N and L may then be computed for a best-fit of the measured second derivative values and known $O_2$Sat and HbT. Alternatively, the measured second derivative values and known $O_2$Sat and HbT may be used to generate a look-up table for converting the measured second derivative values to HbT.

SF is a spacing factor which may be used to adjust for an emitting-to-detecting portion spacing that may be different during tissue measurements than that used during calibration. Since the HbT measurement is dependent on both $O_2$Sat and the measurement volume, and measurement volume is dependent on the optical path of the sensor, defined at least in part by the spacing between the emitting and detecting portions, the HbT measurement needs to be corrected for changes in emitting-to-detecting portion spacing. For example, the sensor may be calibrated using a nominal emitting-to-detecting portion spacing, however when multiple emitting and/or detecting portions are selectable in a sensor or combination of sensors, the spacing may be different during monitoring than that used during calibration. As such, a spacing factor corresponding to selectable emitting-to-detecting portion spacings may be stored and used to correct the HbT measurement when a different spacing is used during monitoring than during calibration.

Once the scaled second derivative is obtained, the stored calibration data is used at block 314 to derive the absolute $O_2$Sat. The second derivative for attenuation at 720 nm wavelength (and 760 nm) is dependent on oxygen saturation and total hemoglobin. Thus, at block 316, HbT may be determined knowing the D"(720) (or D"(760)) with respect to wavelength, the derived absolute $O_2$Sat, and the stored calibration data.

Tissue oxygenation, or the availability of oxygen to tissue, as defined herein, is a function of both tissue $O_2$Sat and HbT. Depending on the particular tissue oxygenation monitoring application, the derived $O_2$Sat and HbT may each be used separately in a monitoring algorithm or combined to determine a tissue oxygenation index used to monitor a patient's status and/or control a therapy. At block 322, a tissue oxygenation index may be computed as a function of $O_2$Sat and HbT. For example, a tissue oxygenation index (TOI) may be a weighted combination of the $O_2$Sat and HbT measurements. In one embodiment, a tissue oxygenation index is computed as:

$$TOI = W_1 O_2 Sat + W_2 HbT \quad (6)$$

wherein $W_1$ and $W_2$ are weighting factors selected for a particular application. may be tailored to an individual patient. It is contemplated that non-linear combinations of $O_2$Sat and HbT may also be used. Furthermore, a heart failure index or score may combine multiple physiological variables with the tissue oxygenation measurements to assess patient condition and/or evaluate response to a therapy.

A tissue oxygenation index computed using absolute measurements of $O_2$Sat and HbT can be available on a continuous or periodic basis. The TOI and/or the individual calibrated values of $O_2$ Sat and HbT may be used for tracking a patient's tissue oxygenation and changes in patient status based on changes in oxygenation.

The absolute values of $O_2$Sat, HbT and the TOI computed using the calibrated absolute values of $O_2$Sat and HbT are computed and stored. Additionally, differences between each of these oxygenation measures and a baseline or other earlier corresponding measure may be computed and stored as calibrated trended variables. As such, in addition to storing the absolute values, trended values of each of the oxygenation measurements may be stored as changes in the absolute values over time, referred to as $dO_2$ Sat, dHbT or dTOI, which each represent the difference between a current measurement and a previous measurement of the same calibrated measurement.

Alternatively or additionally, non-calibrated values and trends of the oxygenation measurements may be determined and stored. Since sensor calibration can be time consuming and computing a calibrated measurement adds to the computational burden of the device, it may be desirable to compute non-calibrated values and trends of oxygenation measurements without conversion of those measurements to an absolute value. For example, a scaled second derivative of a properly selected wavelength, $SD"(\lambda)$, is a volume-independent measure of $O_2$Sat and may be determined as an index of $O_2$Sat without conversion to a calibrated measurement. Likewise, $D"(\lambda)$, which is volume and oxygen dependent, can provide an index of HbT without conversion to a calibrated measurement. Each of these uncalibrated tissue oxygenation measurements may be used individually as baseline indices of tissue oxygenation or combined in a computation of a TOI, such as a weighted linear combination of the uncalibrated measurements similar to Equation (6) above. The uncalibrated measure of $SD"(\lambda)$ used as an $O_2$Sat index is a volume-independent measurement which can provide meaningful measurements at a single time point, or over long- or short-term trends.

The uncalibrated measurements of $SD"(\lambda)$, $D"(\lambda)$, and a TOI computed using $SD"(\lambda)$ and $D"(\lambda)$ may be determined and stored for use as baseline measurements and measured at future time points for monitoring patient status and for use in detecting physiological events and controlling device-delivered therapies. Trends in each of the uncalibrated measurements over time, referred to as $dSD"(\lambda)$, $dD"(\lambda)$, and dTOI, may also be determined and stored as the difference between a current uncalibrated measurement and a previous corresponding measurement. In summary, various algorithms for monitoring tissue oxygenation may utilize calibrated measurements ($O_2$ Sat and HbT), trends in the calibrated measurements ($dO_2$Sat and dHbt), uncalibrated measurements ($SD"(\lambda)$ and $D"(\lambda)$), trends in the uncalibrated measurements ($dSD"(\lambda)$ and $dD"(\lambda)$) or any combination of the foregoing measurements and trends. Furthermore, indices or trends of indices of tissue oxygenation determined using 2- or 3-wavelength sensors may be used.

The oxygen saturation measurement derived from a scaled second derivative is a volume-independent measurement and is therefore expected to have reduced susceptibility to motion artifact, which could alter the optical path of the sensor and thus alter the measurement volume. However, some embodiments may utilize the measured HbT, which is dependent on the measurement volume, to filter or blank tissue oxygenation monitoring during periods in which HbT is out of a normal range, which may be due to motion or activity of the patient.

Accordingly, in one embodiment, the measured HbT is compared to an acceptable range, e.g. between approximately 1% and approximately 25%, at block 318. If HbT is out of the acceptable range, tissue motion may be causing erroneous HbT measurements. At block 320, the tissue oxygenation measurement is blanked or otherwise deemed invalid based on the out-of-range HbT measurement. For example, patient activity may result in oscillatory movements that produce a signal that is intermittently in and out of the acceptable range. Intervals in which the HbT measurement is out-of-range may be blanked for determining a tissue oxygenation index. During intervals in which the HbT measurement is in range, the tissue oxygenation index is computed at block 322. When HbT is out of range, the absolute tissue oxygen saturation measurement may also be ignored or still be determined and stored.

Alternatively, $O_2$Sat and HbT measurements may be filtered based on the fluctuation of HbT. If HbT variability is low, than a low rate of averaging (low pass filtering) $O_2$Sat and HbT measurements may be used. If HbT variability increases, an increasing filtering or averaging frequency may be used based on the increased HbT variability.

Figure 5:
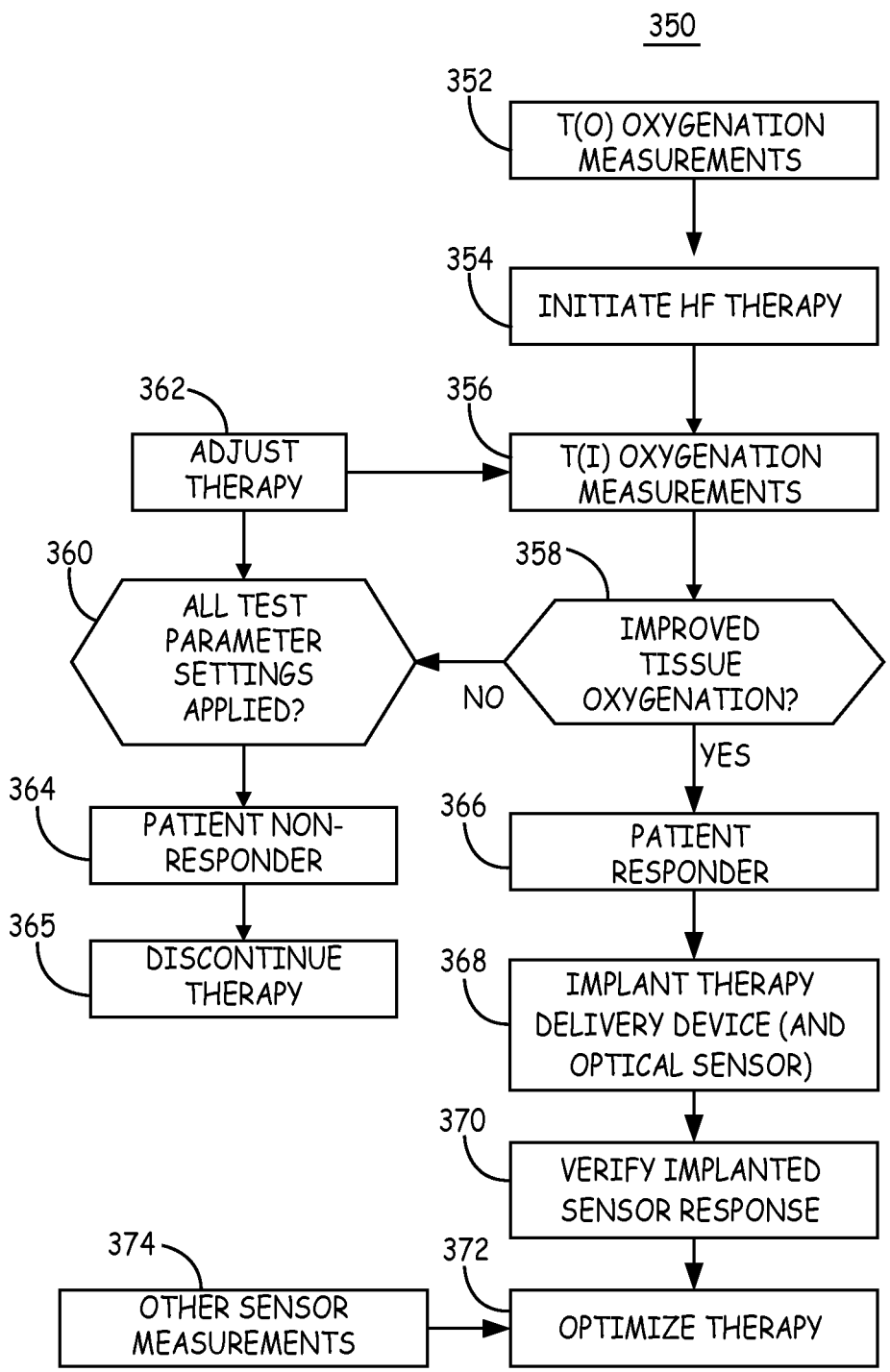
FIG. 5 is a flow chart of a method for evaluating a heart failure patient's response to a therapy using an optical sensor.

FIG. 5 is a flow chart of a method 350 for evaluating a heart failure patient's response to a therapy using an optical sensor. At block 352, baseline tissue oxygenation measurements (T(0) measurements) are obtained in a heart failure patient. In one embodiment, the baseline measurements are obtained using an external optical sensor coupled to an external monitor, e.g. sensor 34 and monitor 36 as shown in FIG. 1.

At block 354, a HF therapy is initiated. In one embodiment, the heart failure therapy is CRT. CRT therapy may be initiated at block 354 during a surgical implant procedure using an IMD (e.g. IMD 10 shown in FIG. 1) capable of delivering CRT, including electrical pacing pulse generation circuitry and cardiac electrodes coupled to the pulse generation circuitry. The IMD senses cardiac signals and is programmed to deliver pacing pulses to one or more heart chambers in timed relation to sensed or paced events in another heart chamber. The IMD delivering the HF therapy may be in wireless communication with an external monitor as generally shown in FIG. 1 to cooperatively acquire tissue oxygenation measurements before and subsequent to initiating HF therapy.

Alternatively, the HF therapy delivered by an IMD may be a cardiac assist therapy, e.g., provided by a co- or counter-pulsation or continuous blood pumping device such as an IABP or LVAD. In other embodiments, the HF therapy delivered by an IMD may be a drug therapy or other biological agent delivered using a catheter and implantable pump.

Alternatively, a HF therapy may be initiated using an external therapy delivery device. The external therapy delivery device may be an external electrical stimulation device, external cardiac assist device or blood pump, or external fluid delivery pump for administering a drug or biological agent. An external therapy delivery device may be coupled as needed to cardiac stimulation electrodes or catheters advanced into the heart or vascular system during a catheterization procedure.

Figure 6:
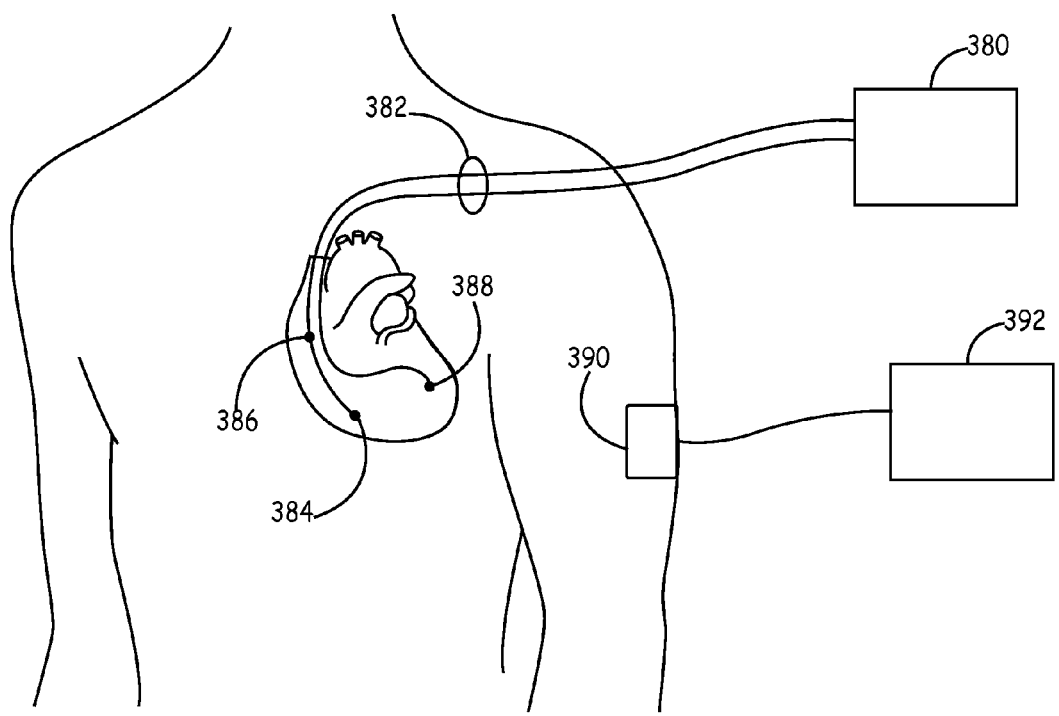
FIG. 6 is a schematic view of an alternative medical device system for use in evaluating a patient's response to a HF therapy.

FIG. 6 is a schematic view of an alternative medical device system for use in evaluating a patient's response to a HF therapy using method 350. Since a fully implantable device for delivering CRT or another HF therapy can be costly and is invasive to implant, an external therapy delivery device 380 may be provided for evaluating the patient's response to a therapy. In this way, if the patient is identified as a non-responder to the therapy, the additional surgical procedure and costs associated with implanting an IMD can be avoided.

In one embodiment, external therapy delivery device 380 is coupled to transvenous leads 382 carrying multiple electrodes 384, 386 and 388 positioned for sensing and stimulating in the right ventricle, right atrium, and/or left ventricle, respectively. The external device 380 includes circuitry for sensing cardiac signals using the electrodes 384, 386 and 388, generating pacing pulses delivered via electrodes 384, 386 and/or 388, and controlling the delivery of the pacing pulses to one or more heart chambers in timed relation to sensed or paced events in another heart chamber.

In other embodiments, the external device may be provided for performing a cardiac assist (blood pumping) therapy or delivering a drug. As such, the external device may alternatively be coupled to catheters as needed for delivering the therapy.

An external optical sensor 390 is positioned to measure tissue oxygenation along an extremity of the patient. Optical sensor 390 is coupled to an external tissue oxygenation monitor 392. Monitor 392 includes control circuitry for controlling light emission by sensor 390 and signal processing circuitry for receiving a sensor output signal and computing a tissue oxygenation measurement. In various embodiments, the external therapy delivery device 380 and the external monitoring device 392 may be provided as a single external unit or may be in wired or wireless communication with each other to cooperatively perform tissue oxygenation measurements prior to initiating a HF therapy, subsequent to initiating a heart failure therapy, and subsequent to adjusting a parameter controlling the heart failure therapy delivery.

Referring again to FIG. 5, tissue oxygenation measurements are obtained subsequent to initiating the heart failure therapy (T(i) measurements) at block 356. A controlled time delay between initiation of the HF therapy and the tissue oxygenation measurements performed at block 356 may be applied to allow a cardiac response to the therapy to occur. Alternatively, tissue oxygenation measurements may be sampled continuously from the time therapy is initiated to a time subsequent to therapy initiation to obtain a time-based plot of tissue oxygenation measurements from therapy onset to some later time point.

Tissue oxygenation measurements may include an absolute $O_2Sat$ and/or HbT, uncalibrated measures thereof, an index computed as a function of $O_2Sat$ and HbT or other non-calibrated indices or trends of tissue oxygenation obtained using an optical sensor measuring the attenuation of two or more light wavelengths. At block 358, the baseline oxygenation measurements are compared to the measurement(s) obtained subsequent to initiating therapy. If tissue oxygenation is improved or exhibiting an increasing trend, e.g. based on an increase in the tissue oxygenation measurement(s) after initiating therapy as compared to the baseline measurements, the patient is identified at block 366 as a responder to the HF therapy. Conversely, tests may also be performed for measuring tissue oxygenation with the therapy on and then turning off or removing the therapy to determine if tissue oxygenation decreases.

If an external therapy delivery device has been used to test the patient's response to therapy, a surgical procedure may be performed to implant an IMD for delivering the HF therapy at block 368. Implantation of the therapy delivery device may include implanting an optical sensor if an external sensor was used to detect the patient response to the HF therapy. The implanted sensor response to tissue oxygenation with the HF therapy on and off may be verified at block 370. Alternatively, an oxygenation measurement using the implanted sensor may be compared to a real time oxygenation measurement acquired using an externally placed sensor to verify the implanted sensor is obtaining a reliable signal for tissue oxygenation monitoring.

The therapy delivery is continued at block 372 and may be further optimized to provide a maximal tissue oxygenation response, using either an external optical sensor or an implanted optical sensor. Optimization of tissue oxygenation may be performed by testing different control parameters, automatically or manually, until a maximum (or targeted) tissue oxygenation is achieved. Additional physiological sensor measurements may be provided as input during therapy optimization as indicated by block 374. Other sensor measurements may include heart rate, posture, activity level, or other physiological sensor signals listed previously herein. Each of these signals may influence an optimal therapy control parameter as well as a targeted tissue oxygenation. For example, one goal of the therapy delivery may be to increase stroke volume and lower a resting heart rate. Therapy control parameters may therefore be adjusted until a reduced heart rate maintains tissue oxygenation within an acceptable range. An oxygenation measurement may be normalized by heart rate such that the normalized measurement is dependent on changes in stroke volume. The therapy delivery is adjusted to maintain or increase the normalized tissue oxygenation measurement, which may then reflect either a reduced heart rate or increased stroke volume or both.

If the tissue oxygenation measurements are not improved at block 358, adjustment of the therapy may be required to obtain a positive response. A determination is made at block 360 if other test parameter settings are available for testing the heart failure therapy response of the patient. As used herein, control parameters relating to a HF therapy can include electrode location relative to the heart, electrode selection, electrical stimulation pulse amplitude (or energy), and timing parameters controlling the timed delivery of pacing pulses in one or more heart chambers relative to sensed and/or paced events in other heart chambers. Thus control parameters can be adjusted by repositioning an electrode relative to the heart tissue, selecting a different electrode (within the same or a different heart chamber) for sensing cardiac signals and/or for delivering stimulation pulses to the heart or to a nerve, e.g. the vagus nerve, adjusting a pacing pulse amplitude, or and adjusting a timing parameter.

The control parameters will depend on the type of therapy being delivered. When a cardiac assist therapy is being delivered, the duty cycle of the pumping function of an IAPB, LVAD or other cardiac assist device may be adjusted. When a drug therapy is being delivered, the dosage may be adjusted.

If additional test parameter settings are available, the HF therapy is adjusted at block 362 by adjusting a therapy delivery control parameter one at a time or in combination with other control parameters. Tissue oxygenation measurements are repeated at block 356 to determine if tissue oxygenation has improved in response to the adjusted therapy.

If test settings available for adjusting the HF therapy have been exhausted, and no improvement in the tissue oxygenation has been measured, the patient is identified as a non-responder to the HF therapy at block 364. The therapy may be discontinued at block 365. An implanted IMD or any associated leads, electrodes or catheters may be explanted or a decision not to implant an IMD for delivering the therapy can be made. In this way, a clinician can make an informed decision as to whether to pursue a particular HF therapy in a patient.

Figure 7:
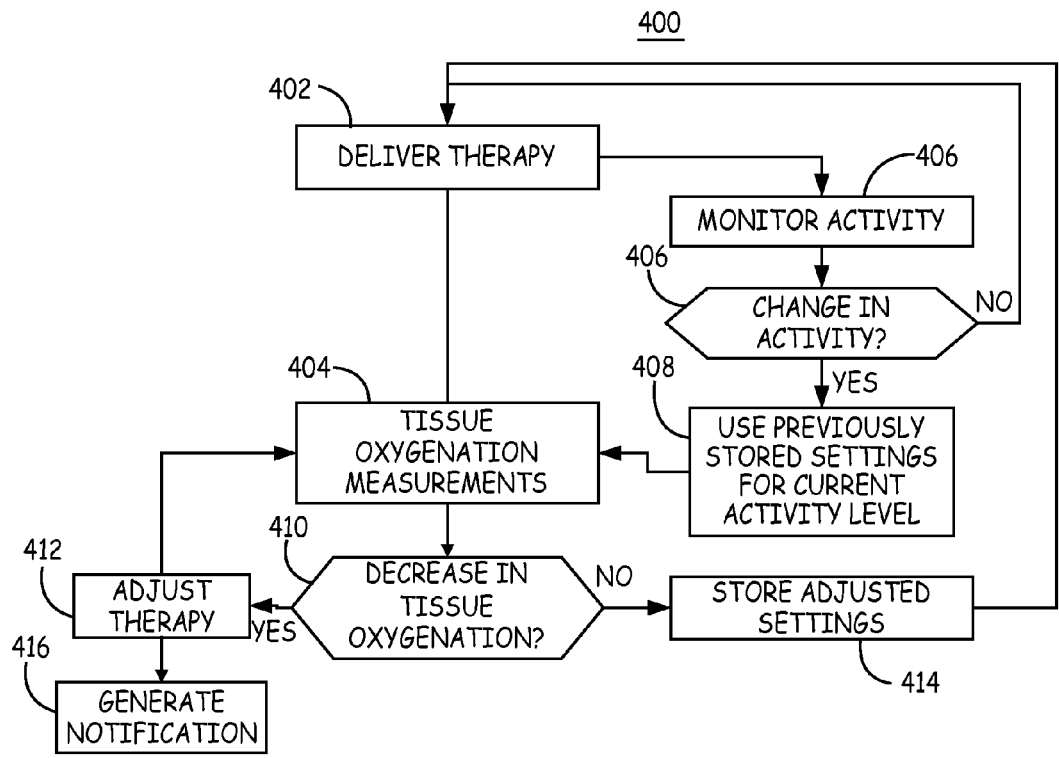
FIG. 7 is a flow chart of a method for managing a HF therapy using tissue oxygenation monitoring.

FIG. 7 is a flow chart of a method for managing a HF therapy using tissue oxygenation monitoring. At block 402 a HF therapy is delivered using an initial set of control parameters (or may be initially turned off). At block 404, tissue oxygenation measurements are performed. Tissue oxygenation measurements may be sampled continuously or performed on a scheduled periodic basis.

Tissue oxygenation measurements taken at block 404 may be performed using an implantable or wearable sensor on a continuously sampled or scheduled periodic basis. Alternatively, periodic tissue oxygenation measurements may be performed at block 404 using an external sensor associated with a home-monitor device or a clinic-based device programmer or monitor.

If the tissue oxygenation has decreased, as determined at block 410, the therapy may be adjusted at block 412. A decrease in tissue oxygenation may be detected at block 410 by comparing a current tissue oxygenation measurement to a threshold value or a previously-defined acceptable normal physiological range. For example, if the tissue oxygenation measurement corresponds to an oxygen saturation of at least approximately 80%, or another threshold, no therapy response may be provided since the oxygenation state is considered to be sufficient. Alternatively, a decrease in tissue oxygenation may be based on a difference with a previous oxygenation measurement, which may be a previously stored measurement, such as an initial baseline measurement, a previous periodic measurement, or a running average. If the current tissue oxygenation measurement is determined to be decreased to a level that tissue oxygenation may be impaired, the therapy is adjusted at block 412.

Therapy adjustments may include turning a therapy on if it was previously off, selecting a different stimulation electrode, different stimulation pulse amplitude, or different pacing timing parameters. Other adjustments may include a drug dosing, blood pump settings, pacing or stimulation duty cycles, or the like. Adjustments to the therapy may continue until an optimal tissue oxygenation is achieved. An optimal tissue oxygenation may be defined as a maximum tissue oxygenation measurement but may alternatively be defined as an oxygenation measurement that falls within an acceptable range or is greater than a predefined threshold. In some cases, selecting optimal HF parameters may take into account other factors such as minimizing cardiac pacing. As such, a "maximum" tissue oxygenation as used herein may be defined as a targeted optimal value or range or a maximum that occurs within limits of the heart failure therapy control parameters, within a predefined acceptable tissue oxygenation range, or within limits of other hemodynamic, metabolic, or physiological measurements. For example, a maximum tissue oxygenation may be the maximum tissue oxygenation that can be achieved when the heart rate is maintained within a predefined resting heart rate range.

It is further contemplated that under some circumstances, tissue oxygenation may be reduced as a side effect of a delivered therapy. As such, therapy adjustment performed at block 412 may include turning a therapy off.

Any adjustments to the HF therapy control parameters in response to detecting a decreased (or subthreshold) oxygenation measurement may be stored at block 414. The adjusted parameter settings are then used to continue HF therapy delivery at block 402.

In some embodiments, a significant drop in tissue oxygenation may cause a notification to be generated at block 416 to notify the patient and/or clinician that low tissue oxygenation has been detected. A threshold applied to an absolute tissue oxygenation measurement or trended measurement that causes a notification to be generated may be defined uniquely from criteria defined for detecting a tissue oxygenation decrease that warrants a therapy adjustment. Since low tissue oxygenation may be predictive of heart failure events, the notification may allow preventative clinical intervention to be taken. A significantly low or out of range tissue oxygenation measurement may also indicate a device-related issue that may need to be addressed by reprogramming, repositioning or replacement of the device.

While method 400 relates primarily to adjusting a heart failure therapy in response to decreasing or low tissue oxygenation, it is contemplated that therapy adjustments may also be made in response to an increasing or high tissue oxygenation measurement. For example, if tissue oxygenation is high and the patient is at rest, the therapy may be reduced or turned off in response to the high tissue oxygenation. Furthermore, a therapy may be adjusted to a minimum level that maintains a stable tissue oxygenation. As such adjustments may be made, for example a duty cycle of CRT therapy may be adjusted, when tissue oxygenation is high or stable within a normal range to determine the minimum amount of CRT pacing required to maintain the tissue oxygenation at a stable level.

In a medical device system that does not include therapy delivery, it is recognized that an implanted or wearable optical sensor may be used for taking tissue oxygenation measurements at block 404 and detecting a significant decrease in tissue oxygenation at block 410. Tissue oxygenation data may be stored in device memory for later review by a clinician. A notification may be generated at block 416 in response to detecting significantly low or decreased tissue oxygen saturation. A tissue oxygen notification allows manual adjustments of a HF therapy to be performed. For example, a clinician may be titrating a HF medication. Notification of a low tissue oxygenation allows a clinician to adjust the HF medication appropriately.

Additionally or alternatively, tissue oxygenation measurements may be performed at block 404 on a triggered basis in response to detecting a change in another monitored physiological signal, e.g. a change in heart rate, blood pressure, patient activity, patient posture or the like. Tissue oxygenation measurements may then be optionally normalized by the physiological measurement, such as activity or heart rate, or different thresholds may be defined for different levels of the triggering physiological signal. For example, as described previously, it may be desirable to maintain or improve tissue oxygenation while lowering or maintaining the heart rate with a corresponding increase in stroke volume. In method 400, patient activity is monitored at block 406. Activity may be monitored for providing a sensor indicated pacing rate and/or for providing a trigger for monitoring tissue oxygenation. A change in activity may trigger tissue oxygenation monitoring at block 404. Alternatively, a change in activity that results in a change in a sensor indicated pacing rate (and thus a heart rate change) may trigger tissue oxygenation monitoring at block 404.

In some embodiments, different HF therapy control parameters may be stored for different activity levels (or different heart rates). As such, if a change in activity is detected, previously stored therapy delivery parameter settings may be used to deliver the HF therapy at block 408.

Tissue oxygenation measurements are obtained at block 404. If a decrease in tissue oxygenation is detected at block 410, the therapy may be adjusted at block 412 until improved oxygenation is achieved. Any adjustments to the HF therapy control parameters may be stored for the current patient activity level (or heart rate) at block 414. Stored parameter settings may be used the next time the patient activity (or heart rate) returns to the current level or range. In particular, if the HF therapy control parameters are found to improve tissue oxygenation, the stored parameters may be used the next time a similar activity level (or heart rate) is measured.

It is recognized that during increased activity, the tissue oxygenation measurements may exhibit a decreasing trend as oxygen is consumed by the tissue. As such, comparisons of the tissue oxygenation measurements performed at block 410 for detecting a decreasing tissue oxygenation may be dependent on the activity level (or heart rate) detected and the time duration of a reduced tissue oxygen saturation. For example, a decreasing tissue oxygenation measurement may be tolerated to some minimum threshold and/or for some minimum period of time period after which therapy adjustments are made. The thresholds or other criteria applied at block 410 for detecting a decrease in tissue oxygenation that results in a therapy adjustment may be defined differently for different levels of activity, e.g. rest, activities of daily living, and more strenuous exercise. The tissue oxygenation measurements may be normalized by activity level (or heart rate) then compared to a threshold instead of using activity or heart rate-dependent thresholds for the comparison performed at block 410 for detecting a decreased tissue oxygenation.

As stated previously, tissue oxygenation monitoring may involve determining absolute measurements of $O_2Sat$ and HbT, determining trends of these measurements, determining indices of oxygenation measurements or trends of indices. As such, the comparison of the tissue oxygenation measurement to a threshold at block 410 may include a comparison of a trend or rate of change of a tissue oxygenation measurement in response to a threshold rate of change. A decreasing trend of a tissue oxygenation measurement may be improved by adjusting the therapy to cause a slower rate of decrease. The threshold used at block 410 may therefore be a threshold rate of decrease, a minimum absolute or indexed threshold, or a time period for tolerating a decreasing tissue oxygenation measurement as mentioned above. By slowing the rate of decrease through therapy adjustment, or altering the decreasing trend upon reaching a minimum threshold or time limit by therapy adjustment, the patient may be able to sustain the current level of activity for a longer period of time. As described previously, the threshold may be a predefined threshold or a threshold based on a previous tissue oxygenation measurement trend. Different thresholds may be defined for different activity levels (or heart rates) or measurements may be normalized by activity level or heart rate.

Alternatively, during activity, it may be desirable to provide a therapy adjustment to improve tissue oxygenation measurement earlier than at rest in order to meet increased metabolic demand and avoid tissue hypoxia. As such, a higher threshold may be applied to tissue oxygenation measurements during exercise than at rest in order to respond earlier by adjusting the HF therapy in an attempt to increase tissue oxygenation to meet metabolic demand. In other words, a smaller decline in tissue oxygenation may be allowed during exercise than at rest since resting tissue may be less likely to become hypoxic when tissue oxygenation is reduced.

In method 400, tissue oxygenation monitoring performed at blocks 404 and 410 and subsequent therapy adjustments may be performed by a wholly implantable system using an optical sensor incorporated in the IMD delivering the HF therapy, an optical sensor coupled to the IMD delivering the HF therapy via a lead, or an implanted optical sensor in wireless communication with the IMD. The optical sensor may be positioned to measure tissue oxygenation at any core body or peripheral location. In some embodiments, the optical sensor is located along an extremity to allow for low peripheral tissue oxygenation to be detected and responded to.

In alternative embodiments, the optical sensor used to perform the tissue oxygenation measurements is an external sensor. An external sensor may be a wireless sensor worn by the patient and in communication with the IMD delivering the HF therapy to allow ambulatory tissue oxygenation monitoring and HF therapy optimization. Alternatively, the external sensor is a wireless sensor in communication with an external monitor in the patient's home or a clinic. A clinician can evaluate tissue oxygenation measurements and adjust the patient's HF therapy using an external programmer. Such monitoring and adjustments may occur remotely using a remote patient management system that includes a networked database receiving tissue oxygenation data for review by the clinician or an expert patient management center.

An external sensor may alternatively be embodied as a wired sensor that is coupled to an external monitor in the patient's home or in a clinic. The patient may instructed to position the sensor for transcutaneous tissue oxygenation measurements on a regular basis, e.g. daily, to allow therapy adjustments to be performed regularly, through an automated medical device system or with manual intervention.

While embodiments described herein relate primarily to managing a device-delivered heart failure therapy, it is further recognized that tissue oxygenation monitoring may be performed in a heart failure patient without including a device-delivered heart failure therapy delivery. For example, IMD 10 in FIG. 1 or an implanted or wireless sensor may be provided for heart failure monitoring. Tissue oxygenation measurements may be stored in memory and/or transmitted to an external monitoring device or remote patient management database for prognostic or diagnostic purposes. For example, tissue oxygenation measurements may be monitored to assess a patient's response to a heart failure medication. A clinician can evaluate the status of the patient's heart failure based on tissue oxygenation measurements to determine if the patient is improving or worsening and adjust a medical regimen accordingly.

For example, tissue oxygenation measurements may be used when titrating a drug therapy for heart failure. One goal in the medical management of a heart failure patient is to lower ventricular filling pressure to prevent pulmonary edema. However, if the filling pressure is lowered too much, cardiac output will drop and the patient will become symptomatic. A challenge faced by clinicians managing heart failure patients is to identify the optimal dosages of medications given to simultaneously manage the patient's heart function and fluid status (edema). By monitoring tissue oxygenation using a medical device system as described herein during the period that the dosing of the medications (e.g. diuretics) is titrated, early feedback is provided to the clinician if tissue oxygenation begins to decrease. A decrease in tissue oxygenation may indicate a decrease in cardiac output, allowing the clinician to respond quickly by adjusting the medication before patient symptoms appear or become severe.

Thus, a medical device and methods for use have been presented in the foregoing description with reference to specific embodiments. It is appreciated that various modifications to the referenced embodiments may be made without departing from the scope of the invention as set forth in the following claims.

The invention claimed is:

1. A method for controlling a therapy in a patient, comprising;
    sensing an activity sensor signal;
    detecting a change in activity level of the patient from the activity sensor signal;
    sensing an optical sensor signal corresponding to tissue light attenuation in a tissue volume;
    computing a tissue oxygenation measurement from the optical sensor signal in response to detecting the change in activity level, the tissue oxygenation measurement comprising contributions from arterial and venous blood in a measurement volume, wherein computing the tissue oxygenation measurement comprises computing a trend;
    detecting a decrease in tissue oxygenation in response to the tissue oxygenation measurement, wherein detecting a decrease in the tissue oxygenation measurement comprises:
    defining a plurality of thresholds for each one of a respective plurality of activity levels,
    selecting one of the plurality of thresholds in response to detecting the change in activity; and
    comparing the tissue oxygenation measurement and the selected one of the plurality of thresholds; and
    adjusting a parameter controlling delivery of the therapy in response to detecting the decreased tissue oxygenation.

2. The method of claim 1, wherein adjusting the parameter comprises adjusting the parameter to cause a change in the trend.

3. The method of claim 1, wherein detecting the change in activity comprises detecting a change that causes an adjustment to a sensor-indicated pacing rate.

4. The method of claim 1, wherein detecting a decrease in the tissue oxygenation measurement comprises:
    defining a plurality of thresholds for each one of a respective plurality of heart rates;
    sensing a cardiac signal;
    measuring a heart rate of the patient in response to the cardiac signal;
    selecting one of the plurality of thresholds based on the measured heart rate; and
    comparing the tissue oxygenation measurement and the selected one of the plurality of thresholds.

5. The method of claim 1, wherein the plurality of thresholds comprises a first threshold corresponding to a first activity level and a second threshold corresponding to a second activity level, the first activity level being a higher level of activity than the second activity level, and the first threshold being greater than the second threshold.

6. The method of claim 1, wherein detecting a decrease in the tissue oxygenation measurement comprises storing a previous tissue oxygenation measurement and comparing the tissue oxygenation measurement and the previous tissue oxygenation measurement.

7. The method of claim 1, further comprising:
    storing a plurality of parameter settings for each of a plurality of activity levels;
    adjusting the parameter by selecting one of the plurality of settings based on the detected change in activity.

8. The method of claim 1, further comprising:
    sensing a cardiac signal;
    measuring a heart rate of the patient in response to the cardiac signal;
    storing a plurality of parameter settings for each of a plurality of heart rates;
    adjusting the parameter by selecting one of the plurality of settings corresponding to the measured heart rate.

9. The method of claim 1, wherein computing the tissue oxygenation measurement comprises:
    measuring one of a current activity level and a heart rate of the patient; and
    normalizing the tissue oxygenation measurement in response to one of the measured activity level and a measured heart rate.

10. The method of claim 1, further comprising:
    comparing the tissue oxygenation measurement and an upper threshold;
    adjusting the parameter to reduce a duty cycle of the therapy in response to the tissue oxygenation measurement being greater than the upper threshold.

11. The method of claim 1, further comprising:
    sensing a cardiac signal; and
    measuring a heart rate of the patient in response to the cardiac signal, wherein adjusting the parameter comprises adjusting the parameter to cause an increase in the tissue oxygenation measurement without increasing the heart rate.

12. A medical device system for delivering a therapy to a patient, comprising:
    a controller to set a therapy delivery control parameter;
    an optical sensor to produce a signal corresponding to tissue light attenuation;
    an activity sensor to produce a signal correlated to an activity level of a patient;
    a memory to store a plurality of thresholds for each one of a respective plurality of activity levels;
    a processor configured to compute an activity measurement from the activity sensor signal, detect a change in activity in response to the activity measurement, compute a tissue oxygenation measurement from the optical sensor signal in response to detecting the change in activity, and detect a decrease in tissue oxygenation in response to the computed tissue oxygenation measurement, the tissue oxygenation measurement comprising contributions from arterial and venous blood in a measurement volume, wherein computing the tissue oxygenation measurement comprises computing a trend, wherein detecting the decrease in tissue oxygenation comprises:
- selecting one of the plurality of thresholds in response to detecting the change in activity; and
- comparing the tissue oxygenation measurement and the selected one of the plurality of thresholds, and wherein the controller adjusts the control parameter in response to the processor detecting the decreased tissue oxygenation.

13. The system of claim 12, wherein adjusting the parameter comprises adjusting the parameter to cause a change in the trend.

14. The system of claim 12, wherein detecting the change in activity comprises detecting a change that causes an adjustment to a sensor-indicated pacing rate.

15. The system of claim 12, further comprising:
- a memory to store a plurality of thresholds for each one of a respective plurality of heart rates; and
- a sensor to sense a cardiac signal, wherein the processor is further configured to measure a heart rate of the patient from the cardiac signal, and wherein detecting the decrease in tissue oxygenation comprises:
  - measuring a heart rate of the patient from the cardiac signal;
  - selecting one of the plurality of thresholds in response to the measured heart rate; and
  - comparing the tissue oxygenation measurement and the selected one of the plurality of thresholds.

16. The system of claim 12, wherein the plurality of thresholds comprises a first threshold corresponding to a first activity level and a second threshold corresponding to a second activity level, the first activity level being a higher level of activity than the second activity level, and the first threshold being greater than the second threshold.

17. The system of claim 12, further comprising a memory to store a previous tissue oxygenation measurement, wherein detecting a decrease in the tissue oxygenation measurement comprises comparing the tissue oxygenation measurement and the previous tissue oxygenation measurement.

18. The system of claim 12, further comprising a memory storing a plurality of control parameter settings for each of a plurality of activity levels,
- the controller adjusting the parameter by selecting one of the plurality of settings based on the detected change in activity.

19. The system of claim 12 further comprising:
- a memory storing a plurality of control parameter settings for each of a plurality of heart rates; and
- a sensor to sense a cardiac signal, wherein the processor is configured to measure a heart rate in response to the cardiac signal, and the controller adjusts the parameter by selecting one of the plurality of settings corresponding to the measured heart rate.

20. The system of claim 12, further comprising a sensor sensing a cardiac signal, wherein computing the tissue oxygenation measurement comprises:
- measuring one of a current activity level from the activity sensor signal and a heart rate from the cardiac signal; and
- normalizing the tissue oxygenation measurement using one of the measured activity level and the measured heart rate.

21. The system of claim 12, wherein the processor is further configure to compare the tissue oxygenation measurement to an upper threshold, and wherein the controller is configured to adjust the parameter to reduce a duty cycle of the therapy in response to the tissue oxygenation measurement exceeding the upper threshold.

22. The system of claim 12 further comprising a sensor to sense a cardiac signal, wherein the processor is further configured to measure a heart rate of the patient, and the controller and the processor are configured to operate cooperatively to adjust the parameter to cause an increase in the tissue oxygenation measurement without increasing the heart rate.

23. A non-transitory computer readable medium having computer executable instructions for performing a method comprising:
- sensing an activity sensor signal;
- detecting a change in activity level of the patient from the activity sensor signal;
- sensing an optical sensor signal corresponding to tissue light attenuation;
- computing a tissue oxygenation measurement from the optical sensor signal in response to detecting the change in activity level, the tissue oxygenation measurement comprising contributions from arterial and venous blood in a measurement volume, wherein computing the tissue oxygenation measurement comprises computing a trend;
- detecting a decrease in tissue oxygenation in response to the tissue oxygenation measurement, wherein detecting a decrease in the tissue oxygenation measurement comprises:
  - defining a plurality of thresholds for each one of a respective plurality of activity levels,
  - selecting one of the plurality of thresholds in response to detecting the change in activity; and
  - comparing the tissue oxygenation measurement and the selected one of the plurality of thresholds; and
- adjusting a parameter controlling delivery of a therapy in response to detecting the decreased tissue oxygenation.

* * * * *